United States Patent
Cilli et al.

(10) Patent No.: US 12,352,746 B2
(45) Date of Patent: Jul. 8, 2025

(54) PEPTIDE-COMPRISING ELECTRODE

(71) Applicants: Oxford University Innovation Limited, Oxford (GB); Universidade Estadual Paulista "Júlio De Mesquita Filho"—UNESP, São Paulo (BR)

(72) Inventors: Eduardo Maffud Cilli, Araraquara (BR); Paulo Roberto Bueno, Araraquara (BR)

(73) Assignees: Oxford University Innovation Limited, Oxford (GB); Universidade Estadual Paulista "Júlio De Mequita Filho"—UNESP, Sao Paulo (BR)

( * ) Notice: Subject to any disclaimer, the term of this patent is extended or adjusted under 35 U.S.C. 154(b) by 1122 days.

(21) Appl. No.: 16/962,958

(22) PCT Filed: Jan. 23, 2019

(86) PCT No.: PCT/GB2019/050183
§ 371 (c)(1),
(2) Date: Jul. 17, 2020

(87) PCT Pub. No.: WO2019/145706
PCT Pub. Date: Aug. 1, 2019

(65) Prior Publication Data
US 2021/0132050 A1 May 6, 2021

(30) Foreign Application Priority Data
Jan. 23, 2018 (GB) .................................... 1801074
Aug. 24, 2018 (GB) .................................... 1813869

(51) Int. Cl.
*G01N 33/543* (2006.01)
*C07K 5/11* (2006.01)
(Continued)

(52) U.S. Cl.
CPC ....... *G01N 33/5438* (2013.01); *C07K 5/1019* (2013.01); *C07K 5/1021* (2013.01);
(Continued)

(58) Field of Classification Search
CPC ............ G01N 27/026; G01N 27/3276; G01N 33/5438; C07K 5/1019; C07K 5/1021; C07K 7/06
See application file for complete search history.

(56) References Cited

U.S. PATENT DOCUMENTS

2012/0315625 A1* 12/2012 Dussault .......... G01N 33/54353
435/5
2012/0321583 A1* 12/2012 Yurkovetskiy ..... A61K 47/6803
525/413
2018/0120250 A1* 5/2018 Crooks ............ G01N 33/54306

FOREIGN PATENT DOCUMENTS

EP       1356296       4/2016
WO   WO 2015/022483    2/2015
(Continued)

OTHER PUBLICATIONS

A. Santos, Redox-tagged peptide for capacitive diagnostic assays, Biosensors and Bioelectronics, 2015(68), p. 281-87. (Year: 2015).*
(Continued)

*Primary Examiner* — C. Sun
(74) *Attorney, Agent, or Firm* — Klarquist Sparkman, LLP

(57) ABSTRACT

The present application relates to an electrode suitable for use in electrochemical sensing of a target species. The electrode comprises a peptide monolayer of defined length and to one end of which are attached both a redox active species and a receptor that is capable of binding to the target
(Continued)

species. Also provided is an electrochemical method of sensing a target species, which involves the use of the electrode.

21 Claims, 2 Drawing Sheets

(51) Int. Cl.
    *C07K 5/113*     (2006.01)
    *C07K 7/06*     (2006.01)
    *G01N 27/02*     (2006.01)
    *G01N 27/327*     (2006.01)

(52) U.S. Cl.
    CPC .............. *C07K 7/06* (2013.01); *G01N 27/026* (2013.01); *G01N 27/3276* (2013.01)

(56) References Cited

FOREIGN PATENT DOCUMENTS

| WO | WO 2016/120606 | 8/2016 |
|----|----------------|--------|
| WO | WO 2017/063074 | 4/2017 |

OTHER PUBLICATIONS

PubChem for lysine and glutamic acid (Year: 2024).*
A. K. Nowinski, Sequences, Structure, and Function of Peptide Self-Assembled Monolayers, Journal of the American Chemical Society, 2012(134), p. 6000-05. (Year: 2012).*
Bueno et al., "Quantum capacitance as a reagentless molecular sensing element," *Nanoscale* 9(40):153692-15370, October 201.
Bueno, "Common Principles of Molecular Electronics and Nanoscale Electrochemistry," *Analytical Chemistry* 90:7095-7106, May 2018.
Fernandes et al., "Label free dox capacitive biosensing," *Biosensors and Bioelectronics* 50:437, 440, Dec. 2013.
Fernandes et al., "Comparing label free electrochemical impedimetric and capacitive biosensing architectures," *Biosensors and Bioelectronics* 57:96-102, Jul. 2014.
Garrote et al., "Field effect in molecule-gated switches and the role of target-to- receptor size ratio in biosensor sensitivity," *Biosensors and Bioelectronics* 127:215- 220, Feb. 2019.
International Search Report and Written Opinion dated May 3, 2019 from PCT/GB2019/050183 (12 pages).
Isidro-Llobet et al., "Amino Acid-Protecting Groups," *Chemical Reviews* 6:2455-2504, Apr. 2019.
Mahmoud et al., "Impedance Method for Detecting HIV-1 Protease and Screening for Its Inhibitors Using Ferrocene-Peptide Conjugate/ AU Nanoparticle/Single-Walled Carbon Nanotube Modified Electrode," *Analytical Chemistry* 80(18):7056-7062, Aug. 2008.
Piccoli et al., "Redox Capacitive Assaying of C-Reactive Protein at a Peptide Supported Aptamer Interface," *Analytical Chemistry* 90(5):3005-3008, Feb. 2018.
Santos et al., "Redox-tagged peptide for capacitive diagnostic assays," *Biosensors and Bioelectronics* 68:281-287, 2015.
UK Search Report dated Jun. 26, 2018 from GB 1801074.4 (1 page).
Scholle et al., "Sequence of the mglB gene from *Escherichia coli* K12: Comparison of wild-type and mutant galactose chemoreceptors," *Mol Gen Genet*, 208(1-2):247 253 (Jun. 1987).

* cited by examiner

PEPTIDE-COMPRISING ELECTRODE

CROSS REFERENCE TO RELATED APPLICATIONS

This is the U.S. National Stage of International Application No. PCT/GB2019/050183, filed on Jan. 23, 2019, which in turn claims the benefit of Application No. GB 1801074.4, filed on Jan. 23, 2018 and Application No. GB 1813869.3, filed on Aug. 24, 2018. These applications are incorporated herein in their entireties.

The present invention relates to a peptide-comprising electrode suitable for use in electrochemical sensing of a target species, as well as an electrochemical method of sensing a target species, which involves the use of this electrode.

BACKGROUND

Electrochemical techniques have been used in a broad range of sensing applications, for example for the detection and quantification of molecules of diagnostic interest in physiological samples, for sensing toxic gases and for monitoring changes in environmental parameters such as humidity.

Electrochemical impedance spectroscopy (EIS) is a technique that monitors changes in capacitance or charge-transfer resistance associated with the changes in the local environment of a suitably modified electrode surface. Such changes can include the binding of substances (e.g. of a target species such as a biomarker) to the electrode surface. EIS is an attractive technique for sensing applications in view, for example, of its constructional simplicity, sensitivity, selectivity and ready applicability within label-free methodologies.

In recent work it has been shown that electrochemical impedance methods can be applied to resolve a range of charge fluctuations within molecular films confined at electrode surfaces. These comprise changes associated with electronic dipole fluctuation and field induced ionic movement and can be resolved by Electroactive Monolayer Capacitance Spectroscopy according to their specific timescales and surface potential dependence. When these molecular films contain a moiety with orbital states that are energetically accessible (redox active) the electron transfer that results to/from the underlying metallic electrode generates a new, and sensitively potential dependent, charging process at this interface. This faradaic capacitance (known as redox capacitance, $C_r$) is not only electrostatic and can be (for high quality molecular films with associated fast rates of heterogeneous electron transfer) hundreds of times greater than the Helmholtz contribution. It has been shown that this $C_r$ signature can be integrated into films which are additionally able to recruit specific targets of interest (such as the antigen partners of antibodies or aptamers). The redox capacitance change can then be used in the establishment of a novel label free biosensing format of high sensitivity, stability and convenience. For more background details, reference can be made, for example, to WO 2015/022483, WO 2016/120606, Biosensors and Bioelectronics 50 (2013) 437-440 and Biosensors and Bioelectronics 57 (2014) 96-102.

One critical factor affecting the performance of EIS systems is the structure of the functionalised electrode bearing the confined molecular film. Optimisation of the electrode has the potential to yield dramatic improvements in sensor capabilities, for example for achieving enhanced limits of detection ("LOD"), sensitivity to minute changes in target species concentration, and/or selectivity to the target species of interest.

In one recent paper (Biosensors and Bioelectronics 68 (2015) 281-287), Santos et al. reported the preparation of a peptide-functionalised electrode and demonstrated that this system could be applied to the detection of CRP protein by EIS. The peptide reagent had the structure Ac-Cys-Ala-Ala-Lys(Fc)-Ala-Ala, where Ac represents an acetylation at the N-terminal cysteine residue and Fc represents a ferrocene redox species attached to the lysine residue via the latter's amino side chain. The EIS electrode comprised a monolayer of this peptide, further functionalised with anti-CRP antibody attached to the peptide via the free carboxylic acid function at C-terminal alanine residue.

There remains a need in the art to provide further improved systems for sensing of a target species, for example that enable further improvements in features such as limit of detection ("LOD"), sensitivity to changes in target species concentration, and/or selectivity to the target species of interest.

SUMMARY OF THE INVENTION

The present inventors have now identified a new peptide-comprising electrode for use in electrochemical sensing, (e.g., electrochemical impedance spectroscopy (EIS) sensing) of a target species. There are numerous advantages associated with the use of a peptide-based receptive surface rather than other monolayers (e.g., alkanethiol monolayers). For example, peptides potentially have advantages when used in complex biological environments through the avoidance of biological matrix effects. The desired peptide reagents can also be routinely synthesised using well-established principles for peptide synthesis, and their structure easily optimised to particular applications simply by appropriate selection of the amino acid building blocks. Still further, the presence of chemically reactive groups at the end of the peptide and in the side groups of certain amino acid residues readily enables the introduction of redox active species and target species receptors for use in electrochemical methods such as EIS methods.

The present inventors have further found that the specific structure of the peptide monolayer in the new electrode enables particularly advantageous biosensing properties, such as very low limits of detection, coupled with high sensitivity and selectivity to the target species of interest. Specifically, the present invention provides:

[1] An electrode for use in electrochemical sensing of a target species, which electrode comprises:
  (i) an electrically conductive substrate;
  (ii) a peptide monolayer comprising a plurality of peptide molecules that are each:
    (a) disposed on the substrate;
    (b) attached to a redox active species; and
    (c) attached to a receptor that is capable of binding to the target species;
  wherein:
    the peptide molecules are each from three to five amino acid residues in length, including a first terminal amino acid residue that is adjacent to the substrate and a second terminal amino acid; and
    the redox active species and the receptor are each attached to the second terminal amino acid.

[2] An electrochemical spectrometer comprising an electrode of the present invention.

[3] Use of an electrode of the present invention for electrochemical sensing of a target species.

[4] An electrochemical method of sensing a target species, which method comprises:
- (A) contacting a carrier medium that may comprise said target species with an electrode of the present invention;
- (B) obtaining one or more electrochemical measurements from said electrode; and
- (C) determining from said electrochemical measurements whether the target species is present in the carrier medium.

Further preferred features and embodiments are described in the accompanying description and the appended claims.

DETAILED DESCRIPTION

Figure 1:
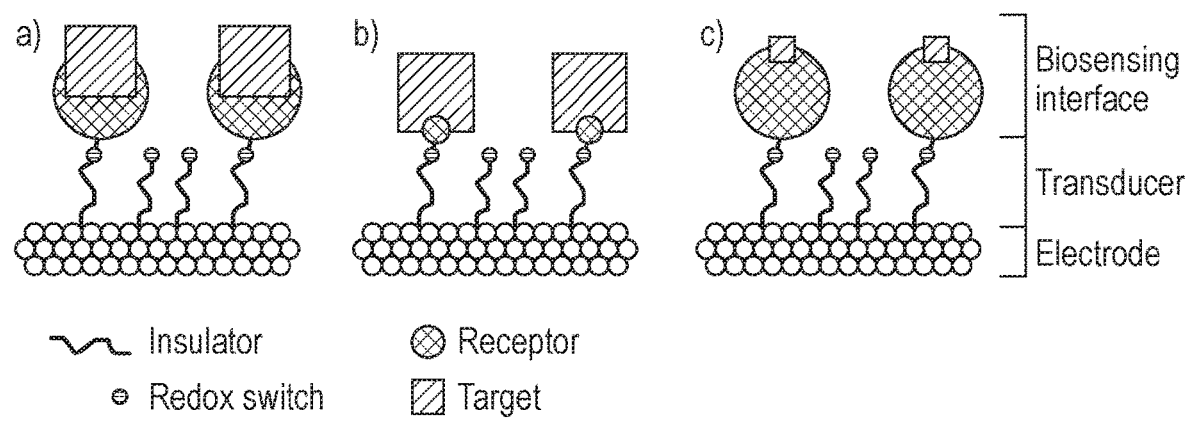
FIG. 1 illustrates schematically various conformations and structural configurations for a functionalised electrode surface having different receptor and target species.

Optional and preferred features of the present invention are now described. Any of the features described herein may be combined with any of the other features described herein, unless otherwise stated.

The Electrode

The electrode functions as the working electrode in an electrochemical system, such as an EIS system.

Electrically Conductive Substrate

The electrode comprises an electrically conductive substrate. This substrate may comprise any electrically conducting material. The substrate may comprise a metal or carbon. The metal may be a metal in elemental form or an alloy of a metal. Optionally, the whole of the substrate comprises a metal or carbon. The substrate may comprise a transition metal. The substrate may comprise a transition metal selected from any of groups 9 to 11 of the Periodic Table. The substrate may comprise a metal selected from, but not limited to, rhenium, iridium, palladium, platinum, copper, indium, rubidium, silver and gold. The substrate may comprise a metal selected from gold, silver and platinum. The substrate may comprise a carbon-containing material, which may be selected from edge plane pyrolytic graphite, basal plane pyrolytic graphite, glassy carbon, boron doped diamond, highly ordered pyrolytic graphite, carbon powder and carbon nanotubes. In a preferred embodiment, the substrate comprises gold, for example the substrate is a gold substrate.

The electrode surface (i.e., the substrate surface) may be planar, which includes a generally flat surface, e.g. without indentations, protrusions and pores. Such substrate surfaces can be readily prepared by techniques such as polishing with fine particles, e.g. spraying with fine particles, optionally in a sequence of steps where the size of the fine particles is decreased in each polishing step. The fine particles may, for example, comprise a carbon-based material, such as diamond, and/or may have particles with diameters of 10 µm or less, optionally 5 µm or less, optionally 3 µm or less, optionally 1 µm or less, optionally 0.5 µm or less, optionally 0.1 µm or less. Following polishing, the substrate surface may be washed, e.g. ultrasonically, optionally in a suitable liquid medium, such as water, e.g. for a period of at least 1 minute, e.g. from about 1 minute to 10 minutes. Optionally, the substrate surface may be washed with an abrasive, e.g. acidic, solution, for example following the polishing and, if used, ultrasonic washing steps. The abrasive solution may comprise an inorganic acid, e.g. $H_2SO_4$, and/or a peroxide, e.g. $H_2O_2$, in a suitable liquid medium, e.g. water. Optionally, the substrates can be electrochemically polished, which may follow any steps involving one or more of polishing with fine particles, washing e.g. ultrasonically and/or using an abrasive solution. The electrochemical polishing may involve cycling between an upper and lower potential until a stable reduction peak is reached, e.g. an upper potential of 0.5 V or more, optionally 1 V or more, optionally 1.25 V or more, and a lower potential of 0.5 V or less, optionally 0.25 V or less, optionally 0.1 V or less.

Peptide Monolayer

The electrode comprises a peptide monolayer comprising a plurality of peptide molecules. The peptide molecules are disposed on the substrate. Typically, the peptide monolyer is a self-assembled monolayer (and hence the peptide molecules are capable of forming a self-assembled monolayer). Typically, the peptide molecules are disposed on the substrate such that they are oriented in the same way, i.e. where the peptide molecules have a first terminal amino acid $A_1$ and a second terminal amino acid $A_2$, then, for each peptide, $A_1$ is adjacent to the substrate and $A_2$ is the amino acid that is furthest from the substrate.

The peptide molecules are each from three to five amino acid residues in length. Preferably, the peptide molecules are each from four to five amino acid residues in length. Most preferably the peptide molecules are each four amino acid residues in length.

The amino acid residues comprised by the peptide are typically alpha-amino acid residues, i.e. they are residues derived from alpha-amino acids of formula $H_2N$—$C(R_1)(R_2)$—$COOH$, where $R_1$ and $R_2$ represent side groups (and where $R_2$ is most commonly, but not necessarily, hydrogen). The amino acid residues may be in the D or L form. Preferably, the amino acids are in the L form unless the D form is specifically identified.

Non-limiting examples of alpha-amino acid residues include the proteinogenic amino acids (e.g., alanine, cysteine, aspartic acid, glutamic acid, phenylalanine, glycine, histidine, isoleucine, lysine, leucine, methionine, asparagine, pyrrolysine, proline, glutamine, arginine, serine, threonine, selenocysteine, valine, tryptophan and tyrosine). Other amino acid residues can also be present, e.g. non-natural amino acid residues. The amino acid residues may also comprise a chemical modification, e.g. they may be a chemically modified derivative of a proteinogenic amino acid. Examples of modifications include natural post-translational modifications (these being well known in the art) and protecting group modifications (i.e. the introduction of a protecting group attached to a chemically reactive group such as a reactive side chain or the amino, amide or carboxylic acid group at the peptide termini, such protecting groups also being well known in the art—see, for example, Chem. Rev. 2009 109 2455-2504).

Each peptide molecule has a first terminal amino acid residue that is adjacent to the substrate and others amino acids to bound to the redox active specie and the receptor. The first terminal amino acid residue may be either the N-terminal amino acid residue or the C-terminal amino acid residue of the peptide. Preferably, the first terminal amino acid residue is the C-terminal amino acid residue.

The first terminal amino acid residue is preferably a cysteine residue, particularly when the electrically conductive substrate comprises gold or is a gold substrate. Cysteine is well known to attach advantageously to gold via its thiol side chain. Thus provisional of a peptide having a terminal cysteine residue provides for ready attachment of the peptides (e.g. by self-assembly) to the substrate.

The first terminal amino acid residue can optionally comprise a chemical protecting group so that it does not comprise a free amine group (where the first terminal amino acid residue is at the N-terminus) or a free carboxylic acid group (where the first terminal amino acid residue is at the C-terminus) that would otherwise be present. Many chemical protecting groups for the N-terminus and C-terminus of peptides are well-known in art (see again, for example, Chem. Rev. 2009 109 2455-2504). One exemplary protecting group for an N-terminal amino acid is an acetyl group (i.e., a —C(O)CH$_3$ group attached to the free amine group). One exemplary protecting group for a C-terminal amino acid is an —NH$_2$ group (i.e. attached to the free carboxylic acid). Such a protected C-terminal amino acid is known as an amidated C-terminal amino acid.

The second terminal amino acid is attached to each of the redox active species and the receptor. Typically the attachment to one of the redox active species and the receptor is via the free amine or carboxylic acid group of the second terminal amino acid. Preferably this attachment is via the free amine acid group of the second terminal amino acid (i.e., in the preferred embodiment where the second terminal amino acid residue is the N-terminal amino acid residue). Most preferably it is the redox active species that is attached via the free carboxylic acid or, most preferably, free amine group of the second terminal amino acid. Typically, the attachment of the other of the redox active species and the receptor (this preferably being the receptor) is via a reactive side group present in the second terminal amino acid. Examples of alpha-amino acids containing suitable such reactive side groups include glutamic acid, lysine, aspartic acid, arginine, histidine, cysteine and tyrosine. Thus, these amino acids constitute preferred second terminal amino acid residues. Particularly preferred are glutamic acid, aspartic acid and lysine, with glutamic acid and aspartic acid being most preferred. In further preferred aspects the second terminal amino acid is selected from glutamic acid and lysine, most preferably glutamic acid.

The peptide contains from one to three non-terminal amino acid residues between the first terminal amino acid residue and the second terminal amino acid. When the peptide molecule is from four to five amino acid residues in length then it contains from two to three non-terminal amino acid residues. When the peptide molecule is four amino acid residues in length then it contains two non-terminal amino acid residues.

The non-terminal amino acids residues can be the same or different. Preferably, the non-terminal amino acids have physically small and/or non-polar side chains so as to promote their stacking in the monolayer and/or the density of peptide molecules in the monolayer. Examples of such amino acids include alanine, glycine, valine, leucine and isoleucine. A preferred non-terminal amino acid residue is alanine. In a particularly preferred embodiment, all non-terminal amino acid residues are alanine residues.

Exemplary peptide molecules have a sequence selected from Glu-Ala-Ala-Cys, Glu-Ala-Ala-Ala-Cys, Lys-Ala-Ala-Cys and Lys-Ala-Ala-Ala-Cys (where the N-terminus is at the first recited amino acid). Such peptides are preferably protected at the C-terminus, e.g. amidated. Thus, particularly preferred peptides include Glu-Ala-Ala-Cys-NH$_2$, Lys-Ala-Ala-Cys-NH$_2$ and Lys-Ala-Ala-Ala-Cys-NH$_2$.

Without being bound by theory, it is considered that the capacity of the peptide to provide particularly beneficial biosensing performance may be connected to the distances that it provides between: (a) the electrode surface and the redox active species; and (b) the redox active species and the receptor. It will be appreciated that these distances arise in consequence of the chain length (three to five, and preferably four, amino acid residues) of the peptide and the attachment of both the redox active species and the receptor to the same amino acid (i.e. the second terminal amino acid). These physical features of the peptide, which may optimise the electronic performance of the electrode, combine with the other advantages of utilising a peptide monolayer rather than other forms of monolayer, as discussed elsewhere herein.

Receptor

The receptor is capable of binding to the target species. As described above, it is attached to the second terminal amino acid of the peptide that is disposed on the substrate.

Preferably, the receptor is capable of specifically binding to the target species. "Capable of specifically binding to the target species" typically means having a binding constant to the target species at least 50 times greater than the binding constant to any other substance(s) present in the carrier medium, preferably at least 100 times greater and more preferably still at least 200 times greater.

Examples of suitable receptors include antibodies, antibody fragments, nucleic acids, aptamers, oligosaccharides, peptides and proteins. Preferably, the receptor is selected from aptamers, antibodies, nucleic acids and peptides. More preferably the receptor is an aptamer or antibody, and most preferably an aptamer.

The antibody or the antibody fragment may be selected from one or more of the classes IgA, IgD, IgE, IgG and IgM. In a preferred embodiment, the antibody or antibody fragment is of the IgG type. The antibody binds selectively to the target species. The antibody or antibody fragment may be derived from a mammal, including, but not limited to, a mammal selected from a human, a mouse, a rat, a rabbit, a goat, a sheep, and a horse. The aptamer may be selected from a peptide aptamer, a DNA aptamer and a RNA aptamer.

Clearly, the choice of receptor for a given electrode is determined by the identity of the target species. For a particular target species, a corresponding receptor that is capable of binding (preferably specifically binding) to the target species should be selected. As one illustrative example, if the target species is dengue NS1 protein (significant blood concentrations of which are associated with dengue virus infection), then the receptor should be a substance capable of binding (preferably specifically binding) to dengue NS1 protein, such as a dengue NS1 antibody.

In a preferred embodiment, the molecular weights (measured, for instance, in kDa) of the receptor and the target species, respectively, are controlled so as to optimise the sensitivity of the electrode for detecting the target species. In particular, it has been found that the range of the field effect giving rise to the sensitivity of the electrode to the presence of a target species can be optimised by decreasing the magnitude of the receptor molecular weight relative to the target species molecular weight, i.e. by increasing the ratio of target species molecular weight to receptor molecular weight. Consequently, low molecular weight receptor species may be preferable for optimising sensitivity, such as for instance via use of aptamer receptors compared with antibody receptors. This effect may at least in part be attributable to a physically smaller, lower molecular weight receptor allowing more intimate access of bound target species to the redox active species and underlying electrode surface. The role of the relative sizes of the target and receptor species is also illustrated schematically in FIG. 1, as discussed in further detail in Example 2.

Thus, the preferred ratio of target species molecular weight to receptor molecular weight ($M_w^{target}/M_w^{receptor}$) may, for instance, be at least 0.5, more preferably at least 1.0, more preferably still at least 10 and particularly preferably at least 25. There is no particular limit on the upper limit of preferred ratio of target species molecular weight to receptor molecular weight, but a notional practical upper limit may for instance be of the order of not more than 1000, e.g. not more than 500 or not more than 200.

Redox Active Species

As described above, the redox active species is attached to the second terminal amino acid of the peptide that is disposed on the substrate.

There is no particular limitation on the identity of the redox active species. However, examples of suitable redox active species include a metallic chemical complex comprising a transition metal such as Fe, Ru, Ti, V, Mn, Cr, Co, Ni, Nb or Mo, or methylene blue. Further representative examples of suitable redox active species include osmium-based redox systems, ferrocenes, quinones and porphyrins, including derivatives thereof. Derivatives of quinine include p-benzoquinone and hydroquinone. Preferably the redox active species is ferrocene or a derivative thereof, for example an alkyl (e.g., $C_{1-6}$ alkyl) or acyl derivative thereof. Most preferably the redox active species is a ferrocene.

Use of the Electrode

The electrode can be used electrochemical impedance spectroscopy (EIS) sensing of a target species. For example, one suitable EIS method of sensing a target species, comprises: (A) contacting a carrier medium that may comprise said target species with an electrode of the present invention; (B) obtaining one or more electrochemical measurements from said electrode; and (C) determining from said electrochemical measurements whether the target species is present in the carrier medium.

The electrode can be applied to methods that are already known in the art for EIS sensing of a target species. Such methods are described, for example, in WO 2015/022483, WO 2016/120606, Biosensors and Bioelectronics 50 (2013) 437-440 and Biosensors and Bioelectronics 57 (2014) 96-102, the contents of which are herein incorporated by reference in their entirety. The present application is not a primer on this subject. Nonetheless, for ease of understanding one exemplary such EIS method, as previously disclosed in WO 2016/120606, is described in more detail below.

Electrochemical impedance spectroscopy (EIS) is a technique that is known to the skilled person. Generally, a varying ac potential is applied on a bias (or DC) potential between a working electrode and a counter electrode. Conventionally, EIS involves scanning across a range of ac frequencies ω. The ratio of the input signal (typically the varying potential) to the output signal (typically the varying current) allows the impedance to be calculated. There is generally a phase difference between the input signal and the output signal, such that the impedance can be considered as a complex function $Z^*$, having a real part (sometimes termed $Z'$) and an imaginary part (sometimes termed $Z''$).

The frequency range of the varying ac potential applied may be from 1 mHz to 10 MHz. The amplitude of the applied ac potential, which is typically in the form of a sine wave, may be from 1 mV to 100 mV, optionally from 5 mV to 50 mV, optionally from 5 mV to 20 mV, optionally from 5 mV to 15 mV, optionally 8 mV to 12 mV, optionally about 10 mV.

When conducting an EIS measurement, the bias potential (or direct current potential) may be set at any desired value. This DC or bias potential is known herein as the applied potential. An exemplary method of the present invention involves obtaining a plurality of measurements of the complex impedance across a range of applied potentials (which allows for the subsequent integration over applied voltage), i.e. a number of EIS measurements are obtained each at different selected voltages. Typically the plurality of measurements of the complex impedance obtained by EIS is at least three measurements, preferably at least five measurements, such as at least ten or even at least twenty measurements, i.e. the range of applied potentials typically comprises at least three different applied potentials, preferably at least five different applied potentials, such as at least ten or even at least twenty different applied potentials.

In the step of converting the plurality of measurements of $Z^*$ into a plurality of measurements of the real component of the complex capacitance, $C'$, measurements of $C'$ at a (fixed/single) selected frequency ω are used. As would be well known to a skilled person $C'$ typically varies as ω changes (i.e. $C'$ is a function of co). The appropriate selected frequency ω will of course depend on the construction of a particular electrode and on the nature of the sensing method being undertaken. However, determination of a suitable selected frequency ω is routine. The skilled person could easily, for example, identify a value of ω where the obtained values of $C'$ are satisfactorily high (e.g. at or close to the maximum value of $C'$ across the frequency range applied in a routine EIS scan) and/or responsive to the particular characteristic of the electrode's local environment that one is seeking to probe. Analogous principles apply when the plurality of measurements of $Z^*$ are converted into a plurality of measurements of the imaginary component of the complex capacitance, $C''$.

Conversion of $Z^*$ at the selected frequency ω into $C'$ and/or $C''$ is routine and well known in the art. In particular, in a standard practical EIS analysis, the complex impedance function $Z^*(w)$ at a particular potential can be converted phasorially into complex capacitance $C^*(w)$ with its real and imaginary components, using the equation $C^*(\omega) = 1/i\omega Z^*(\omega)$.

Integration of the measurements of $C'$ and/or $C''$ as a function of applied voltage can also be routinely performed, for example using "area under the graph methods" when $C'$, $C''$ or any combination of $C'$ and $C''$ is plotted against applied voltage and/or by way of well known and routine computerised algorithms for integrating empirically derived data.

Integration of either $C'$ and $C''$ at the selected frequency ω as a function of applied voltage provides an "integrated measurement value" that is suitable for sensing. Specifically, an integrated measurement value derived from the integration of $C'$ is related to the density of states (DOS) of the system, i.e. it reflects the quantum capacitance. An integrated measurement value derived from the integration of C" is related to the conductance of the system.

In practice, it may sometimes be preferable (for pure simplicity of operation) to obtain the integrated measurement value by integration of only one of C' and C" at the selected frequency ω as a function of applied voltage. In a first preferred embodiment, therefore, the plurality of measurements of Z* is converted into a plurality of measurements of the real component of the complex capacitance, C' at the selected frequency ω and these measurements are converted as a function of applied voltage to obtain the integrated measurement value. Further, in a second preferred embodiment, the plurality of measurements of Z* is converted into a plurality of measurements of the imaginary component of the complex capacitance, C" at the selected frequency ω and these measurements are converted as a function of applied voltage to obtain the integrated measurement value.

However, since both C' and C" can be used, it will also be apparent to the skilled person that an integrated measurement value can be obtained by integrating any combination of C' and C", at the selected frequency ω as a function of applied voltage. For example, any sum of the values of C' and C" (where C' and/or C" are possibly weighted with any negative or positive constants) or any multiple or quotient of the values of C' and C" can be used.

The integrated measurement value is typically compared with one or more reference values. The reference value(s) can be obtained by obtaining one or more corresponding integrated measurement values under conditions where the concentration of the target species is already known. In other words, the reference value(s) are used to calibrate the integrated measurement value obtained when the method is performed under test conditions with expected values that would be obtained under specific, known conditions. Calibration of an apparatus for use in sensing applications is well known and routine in the art, including in methods that are based on EIS.

In step (A) of the method of the present invention, a carrier medium that may comprise said target species is contacted with an electrode of the present invention. The electrochemical response of the system is sensitive to the presence of the target species. Thus, if the carrier medium does contain the target species then a particular integrated measurement value will be obtained. The integrated measurement value will be different if the carrier medium does not contain the target species. Similarly, changes in the integrated measurement value will occur as the concentration of the target species in the carrier medium changes.

The carrier medium is preferably in liquid form although gaseous media are also be possible. The carrier liquid (or gas) may be any liquid (or gas) in which the target species can be suspended or dissolved (or dispersed). In an embodiment, the carrier liquid comprises water. In an embodiment, the carrier liquid comprises a biological fluid. A biological fluid may be a fluid that has been obtained from a subject, which may be a human or an animal. In an embodiment, the carrier liquid comprises an undiluted biological fluid. An undiluted biological fluid in the present context is a biological fluid obtained from a subject, e.g. a human or animal, that has not been diluted with another liquid. The biological fluid may be selected from blood, urine, tears, saliva, sweat, and cerebrospinal fluid. Optionally, the carrier medium comprises a biological fluid obtained from a subject, e.g. a human or animal, and a diluent. The diluent may be added to the biological fluid after it has been obtained from the subject. The diluent may include a liquid medium, e.g. a liquid medium selected from water and an alcohol, e.g. an alcohol, e.g. ethanol. The carrier medium may further comprise a buffer. The buffer may comprise a phosphate.

The target species is a substance that may or may not be present in the carrier medium, optionally together with one or more other non-target species, and which the users wishes to detect/sense. Most typically the method is one for determining the concentration of said target species in said carrier medium.

Although this method can be used to detect a range of target species, one particularly useful aspect is the detection of a species of diagnostic interest. The sensitive detection of biomarkers in physiological samples is of ever growing interest in diagnosis. The methods of the present invention can be used in order sensitively and selectively to sense (and determine the concentration) of specific biomarkers, specifically by providing an electrode substrate that is functionalised with receptor moieties that are capable of specifically binding to the biomarker of interest.

Examples of target species include those selected from the group consisting of CRP protein, insulin and a marker of one or more of neurodegeneration, cancer, myocardial infarction, diabetes and general trauma.

More generally, suitable target species for detection in accordance with the methods of the invention include proteins, polypeptides, antibodies, nanoparticles, drugs, toxins, harmful gases, hazardous chemicals, explosives, viral particles, cells, multi-cellular organisms, cytokines and chemokines, ganietocyte, organelles, lipids, nucleic acid sequences, oligosaccharides, chemical intermediates of metabolic pathways and macromolecules. In preferred embodiments, the target species comprises, consists essentially of, or consists of, a biological molecule, more suitably a biological macromolecule, most suitably a polypeptide. A biomarker is one example of a biological molecule of particular interest.

If the target species is or comprises a protein, the protein may be selected from, but is not limited to, native proteins, denatured proteins, protein fragments, and prokaryotically or eukaryotically expressed proteins. Protein may have its normal meaning in the art, and most preferably 'protein' refers to a polypeptide molecule. Such polypeptide may comprise modifications such as glycosylation; phosphorylation or other such modifications.

If the target species is an antibody, the antibody may be selected from one or more of the classes IgA, IgD, IgE, IgG and IgM.

If the target species is a nanoparticle, the nanoparticle can be selected from, but is not limited to, one or more of insulating, metallic or semiconducting nanoparticles.

If the target species is a drug, the drug may be selected from, but is not limited to, alcohol (e.g. ethanol), amphetamines, amyl nitrate, heroin, ketamine, anabolic steroids, LSD, solvents, *cannabis*, cocaine (such as cocaine hydrochloride or 'coke'), tobacco, tranquilisers, crack (i.e. cocaine free base), ecstasy and/or gammhydroxybutyrate (GHB). Alternatively, in some embodiments, the drug may be a medicinal substance.

The target species may be a candidate drug, e.g. a chemical or biological entity that may be tested or screened for a particular activity or property using the present invention.

If the target species is a toxin, the toxin may be selected from, but is not limited to, one or more toxins originating from animals, plants, or bacteria.

If the target species is a viral particle, the viral particle may be selected from, but is not limited to, one or more viral particles with and without a genome.

If the target species is a cell, the cell may be selected from, but is not limited to, one or more of pluripotent progenitor cells, human cells (e.g. B-cells, T-cells, mast cells, phagocytes, neutrophils, eosinophils, macrophages, endothelial cells), cancerous cells (e.g. those originating from liver, cervical bone, pancreatic, colorectal, prostate, epidermal, brain, breast, lung, testicular, renal, bladder cancers), unicellular organisms of non-human origin, algae, fungi, bacteria, plant cells, parasite eggs, plasmodia and *mycoplasma*.

If the target species is an organelle, the organelle may be selected from, but is not limited to, one or more of nucleus, mitochondria, Golgi apparatus, endoplasmic reticulum, lysosome, phagosome, intracellular membranes, extracellular membranes, cytoskeleton, nuclear membrane, chromatin, nuclear matrix and chloroplasts.

If the target species is a lipid, the lipid may be selected from, but is not limited to, one or more of signalling lipids, structural lipids, phospholipids, glycolipids and fatty acids.

If the target species is nucleic acid sequence, the nucleic acid sequence may be selected from, but is not limited to, one or more of DNA, cDNA, RNA, rRNA, mRNA, miRNA and tRNA.

If the target species is an oligosaccharide, the oligosaccharide may be selected from, but is not limited to, one or more of oligosaccharides of human, animal, plant, fungal or bacterial origin.

The target species may be any antigen or analyte that is indicative of a particular disease. The target may be selected from, for example, dengue NS1 protein, C-reactive protein (CRP protein), angiotensin I converting enzyme (peptidyl-dipeptidase A) 1; adiponectin; advanced glycosylation end product-specific receptor; alpha-2-HS-glycoprotein; angiogenin, ribonuclease, RNase A family, 5; apolipoprotein A-1; apolipoprotein B (including Ag(x) antigen); apolipoprotein E; BCL2-associated X protein; B-cell CLL/lymphoma 2; complement C3; chemokine (C—C motif) ligand 2; CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, clade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like. Markers useful for diabetes include for example C-reactive protein; glucose; insulin; TRIG; GPT; HSPA1 B; IGFBP2; LEP; ADIPOQ; CCL2; ENG; HP; IL2RA; SCp; SHBG; and TIMP2. Currently preferred target species include a target species selected from the group consisting of CRP protein, insulin and a marker of one or more of neurodegeneration, cancer, myocardial infarction, diabetes and general trauma. Another exemplary target species is dengue NS1 protein.

The target species may, for instance, comprise or consist of alpha-synuclein (α-sync).

The target species may be a target associated with monitoring diabetes. In an embodiment, the target may be selected from glucose, insulin, Interleukin 2 receptor alpha (IL2-RA), C-reactive protein (CRP) and glycated hemoglobin (HbAlc). If the target species is glucose, the receptor moieties may be selected from, for example, the molecular recognition element of GDH-FAD assay or a glucose/galactose binding protein ("GGBP") (Scholle, et al., Mol. Gen. Genet 208:247-253 (1987)). If the target is IL-2RA, the receptor moieties may comprise or consist of a monoclonal antibody specific for IL-2RA. If the target species is or comprises C-reactive protein, preferably this is human C-reactive protein. If the target species is or comprises C-reactive protein, the receptor moieties may comprise or consist of anti-CRP. If the target species is or comprises insulin, the receptor moieties may comprise of consist of an insulin antibody.

Examples of specific target species currently of particular interest include an antigen or analyte selected from the group consisting of angiotensin I converting enzyme (peptidyl-dipeptidase A); adiponectin; advanced glycosylation end product-specific receptor; alpha-2-HS-glycoprotein; angiogenin, ribonuclease, RNase A family, 5; apolipoprotein A-1; apolipoprotein B (including Ag(x) antigen); apolipoprotein E; BCL2-associated X protein; B-cell CLL/lymphoma 2; complement C3; chemokine (C—C motif) ligand 2; CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, clade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like. Markers useful for diabetes include for example C-reactive protein; glucose; insulin; TRIG; GPT;

HSPA1 B; IGFBP2; LEP; ADIPOQ; CCL2; ENG; HP; IL2RA; SCp; SHBG; and TIMP2.

Although electrochemical impedance spectroscopy (EIS) sensing of a target species represents a representative and exemplary application of the electrode of the invention, the electrode can also be applied to other uses, methods and apparatuses. For instance, impedance is a time-dependent technique based on a sinusoidal wave perturbation. Thus, other time-dependent techniques can be used as an alternative to impedance. One example of such an alternative technique is square-wave voltammetry, which is a time-dependent technique based on a square wave perturbation.

Thus, the present invention also extends more generally to the use of the electrode of the invention for electrochemical sensing of a target species, for example using a time-dependent electrochemical technique (including, but not limited to, square-wave voltammetry). The present invention also extends generally to an electrochemical method of sensing a target species, which method comprises: (A) contacting a carrier medium that may comprise said target species with an electrode; (B) obtaining one or more electrochemical measurements from said electrode; and (C) determining from said electrochemical measurements whether the target species is present in the carrier medium. The electrochemical measurements may be impedance measurements or other time-dependent electrochemical measurements (including, but not limited to, square-wave voltammetric measurements). For the avoidance of doubt, exemplary target species, carrier media, and the like in relation to these uses and methods are as discussed elsewhere herein.

Apparatus

The present invention also provides an apparatus for use in a sensing method, typically a sensing method of the present invention. This apparatus comprises an electrochemical spectrometer comprising the working electrode as described herein.

The apparatus optionally further comprises (a) a receiver configured to receive, from said electrochemical spectrometer, input data comprising a plurality of measurements of complex impedance, $Z^*$, across a range of applied potentials; and (b) a processor configured to (i) convert said plurality of measurements of $Z^*$ into a plurality of measurements of the real and/or imaginary component of the complex capacitance, $C'$ and/or $C''$, at a selected frequency $\omega$, and (ii) integrate said measurements of $C'$, $C''$ or combination of $C'$ and $C''$, at the selected frequency $\omega$ as a function of applied voltage to obtain an integrated measurement value. The receiver and processor can be part of a computer. The functionality of the receiver and processor can be achieved by programming the computer to receive input data from the method of the invention and to process these data into an integrated measurement value as described herein.

The receiver can receive the input data either directly from the spectrometer, or indirectly, for example by reading the data from a data file created by the spectrometer.

By "programming" it is meant that the computer is provided with computer-readable code providing instructions for carrying out the steps of receiving the input data, converting into real and/or imaginary parts of complex capacitance, $C'$ and/or $C''$, and integrating to obtain an integrated measurement value in an automatic fashion, e.g. without intervention from a user. The computer may for example comprise a physical computer that is programmed with a suitable computer program. That program could, for example, be provided on a storage medium for implementation by the computer, or a network of computers. The storage medium could be an integral part of the computer itself, such as a hard disc, or a removable storage medium such as an optical disc or portable storage device such as a USB flash memory device.

The apparatus can thus be used to carry out a method of the present invention, whereby an operator conducts the necessary (e.g., EIS) measurements of step (A) of the method of the invention using the electrochemical spectrometer and wherein the subsequent steps are then automatically performed to complete the sensing method.

The computer may be further programmed to output data generated from said integrated measurement value. That output may be to a display and/or to a computer file and/or as a data stream to another device. Such data may comprise simple numerical data corresponding to the integrated measurement value itself. Alternatively, the data may comprise an indication of the presence, absence or concentration of a substance being sensed or a qualitative or quantitative indication of a sensed environmental parameter in the system under study. As will be evident to the skilled person, the computer can routinely be programmed to provide such data by additionally programming it with calibration (reference) values relating to the integrated measurement value.

Still further, the invention provides a storage medium storing computer readable code. When implemented, this code is capable of causing a receiver and processor as defined herein (i.e., as a computer as explained above) to perform the steps associated with the receiver and processor in the apparatus of the present invention.

EXAMPLES

Example 1: Peptide-Based Electrodes for Biosensing by EIS

Chemical Reagents

Ultra-pure water was obtained from a Milli-Q 18.2 MΩ×cm system and was used in all solutions. Fmoc-Cys (Trt)-OH, Fmoc-Ala-OH, Fmoc-Glu(OtBu)-OH, Rink Amide resin and 3-ferrocenylpropionic anhydride were purchased from AAPPTEC and Sigma Aldrich Co. (USA). All solvents and chemicals used were of analytical grade.

Electrochemical Apparatus

An Autolab potentiostat equipped with an FRA32 module (METROHM Instruments) was used for electrochemical measurements. A three-electrode setup was used for the measurements consisting of a 2.0 mm diameter gold working electrode from METROHM, a platinum mesh counter electrode, and a silver/silver chloride (Ag|AgCl, filled with 3.0 M KCl) reference electrode. All potentials reported are relative to a Ag|AgCl reference electrode.

Synthesis of Redox-Tagged Peptides

The various peptides were manually produced by solid phase peptide synthesis (SPPS) using Fmoc protocols on Rink Amide Resin (0.48 mmol g$^{-1}$).

Coupling was performed at a 2-fold molar excess relative to the amino component in the resin, using diisopropylcarbodiimide (Dic)/1-hydroxybenzotriazole (HOBt). Fmoc groups were deprotected using 20% 4-methylpiperidine/dimethylformamide (DMF) for 1 and 20 min. For peptides of the invention, the ferrocene redox probe was introduced at the N-terminus by reaction with one molar equivalent 3-ferrocenylpropionic anhydride in 5 mL DCM/DMF (1:1) for 24 h. Peptide cleavage from the resin and removal of the side chain protecting groups were performed with 94% TFA, 2.5% 1,2-ethanedithiol, 2.5% H$_2$O and 1% triisopropylsilane for 2 h. After this, the peptide was precipitated with diethyl ether, separated from soluble non peptide material by centrifugation. The residue was extracted in a 1:1 mixture of solvent A (0.045% (v/v) TFA/H$_2$O) and solvent B (0.036% (v/v) TFA/ACN) and lyophilized. The crude product was purified by HPLC on a Beckman System Gold using a semi-preparative reverse phase Phenomenex Jupiter C18 column (250×10 mm), packed with spherical 5 μm particles and 300 Å pore size. A linear gradient elution was employed from 20 to 50% of solvent B for 90 min. The flow rate was 5 mL min$^{-1}$ at room temperature and the injection volume was 5 mL; UV detection was carried out at 220 nm. The purity of peptide was confirmed using an analytical Shimadzu system with a reverse phase Phenomenex Jupiter C18 column (150×4.6 mm), packed with spherical 5 μm particles and 300 Å pore size, using a linear gradient of 5 to 95% of solvent B for 30 min, a flow rate of 1.0 mL min$^{-1}$ and UV detection at 220 nm. The identity of the peptide was analyzed in an ion-trap Mass Spectrometer using a Brucker system in positive mode, confirming the peptide molecular weight of 635 g/mol.

Electrode Pre-Treatment

Gold electrode surfaces were prepared by mechanical polishing with aluminium oxide pads with particle of size of 0.05 μm. Electrodes were electrochemically polished in 0.5 M NaOH between −0.7 V and −1.7 V (500 cycles). The electrodes were immersed in EtOH under stirring for 20 min. A series of wider range scans, from −0.1 to 1.4 V, were then conducted in 0.5 M H$_2$SO$_4$ at a scan rate of 0.1 V s-1. The reduction peak of the gold oxide layer formed in the anodic scan was used to calculate the real electroactive area of the electrode (subsequently used in normalization).

Sensor Construction

The sensor was prepared by immersion of the clean Au electrodes in a solution containing 2 mM of redox-tagged peptide in H$_2$O/ACN (1:1) for 16 h (25° C.). After being thoroughly rinsed with deionized water, the carboxyl groups of the glutamic acid side chain were activated with N-(3-dimethylaminopropyl)-N'-ethylcarbodiimide 0.4 M (EDC)/ 0.1 M N-hydroxysuccinimide (NHS), using an aqueous solution for 30 min. The modified electrodes were then incubated in 1 μM anti-CRP antibody in PBS (solution) (pH 7.4) for 1 h at room temperature; afterwards CV and EIS were performed to confirm the antibody immobilization. For the peptide containing Lys, after being thoroughly rinsed with deionized water, the carboxyl groups of the anti-CRP were activated with N-(3-dimethylaminopropyl)-N'-ethylcarbodiimide 0.4 M (EDC)/0.1 M N-hydroxysuccinimide (NETS), using an aqueous solution for 30 min. The modified electrodes were then incubated in 1 μM anti-CRP antibody in PBS (solution) (pH 7.4) for 1 h at room temperature; afterwards CV and EIS were performed to confirm the antibody immobilization. The final step involved incubation in 0.1% BSA solution for 30 min to deactivate any remaining active carboxyl groups.

A calibration curve was obtained by immersion of the biosensor in PBS (pH 7.4) containing increasing, specific quantities of CRP ranging from 10 pM to 10 nM. The incubation time was 30 min for each concentration and the electrodes were washed with PBS solution before electrochemical analysis. The relative response at various concentrations of CRP was defined as:

$$RR\%_{CRP}=((RR_{CRP}-RR_{Blank})\div RR_{Blank})\times 100,$$

where RRCRP is the inverse of redox capacitance (1/C$_r$) at a specific concentration of CRP. To evaluate the interfacial specificity, the biosensor was incubated in HSA (1 mM) solution for 30 min and the redox capacitance measured.

Electrochemical Measurements

All electrochemical measurements were carried out in a cell containing 20 mM TBAClO$_4$ supporting electrolyte dissolved in acetonitrile and water (1:4 (v/v)). CV was performed at a scan rate of 100 mV s$^{-1}$ between 0.0 V and 0.7 V relative to Ag|AgCl. Electrochemical impedance measurements were carried out in the AC frequency range of 100 kHz to 0.1 Hz with 10 mV amplitude (peak to peak). The DC bias potential was set to the formal potential of the ferrocene redox-tagged peptide (0.36 V, determined by CV). Measurements were verified for compliance with Kramers-Kronig linear systems theory. Impedance-derived capacitance spectroscopy was performed by determining the capacitance, using the relationship $$C^*(\omega)=1/i\omega Z^*(\omega),$$

where ω is the angular frequency and i is $\sqrt{(-1)}$.

Results and Discussion

Electrodes were functionalised using a range of different peptides to form the SAM. The functionalised electrodes were then subjected to EIS measurements (using CRP as a representative target species, utilising anti-CRP antibody as receptor) to assess their respective performance for biosensing applications. The results are summarised in Table 1.

TABLE 1

Comparison between performance of electrodes based on different peptides

| Peptide structure | Sensitivity per decade (%) | Limit of Detection (nM) | K$_a$ |
|---|---|---|---|
| Ac-Cys-Ala-Ala-Lys(Fc)-Ala-Ala-COOH | 4.0 ± 0.3 | 0.80 | (1.4 ± 0.2) × 10$^8$ |
| Fc-Lys-Ala-Ala-Cys-NH$_2$ | 10.50 ± 2.30 | 0.31 ± 0.24 | (4.8 ± 0.3) × 10$^8$ |
| Fc-Glu-Ala-Ala-Ala-Cys-NH$_2$ | 3.70 ± 0.90 | 0.30 ± 0.03 | (1.7 ± 0.3) × 10$^8$ |
| Fc-Glu-Ala-Ala-Cys-NH$_2$ | 11.40 ± 1.10 | 0.24 ± 0.02 | (5.9 ± 0.3) × 10$^8$ |

In Table 1, Fc refers to a ferrocene redox active species. Anti-CRP antibody was, in each case, attached to the non-cysteine terminal amino acid residue (i.e., Ala in Ac-Cys-Ala-Ala-Lys(Fc)-Ala-Ala-COOH, Lys in Fc-Lys-Ala-Ala-Cys-NH$_2$ and Glu in each of Fc-Glu-Ala-Ala-Cys-NH$_2$ and Fc-Glu-Ala-Ala-Ala-Cys-NH$_2$). Ac-Cys-Ala-Ala-Lys(Fc)-Ala-Ala-COOH corresponds to the peptide described by Santos et al. in Biosensors and Bioelectronics 68 (2015) 281-287). The limit of detection achievable for all of Fc-Lys-Ala-Ala-Cys-NH$_2$, Fc-Glu-Ala-Ala-Cys-NH$_2$ and Fc-Glu-Ala-Ala-Ala-Cys-NH$_2$ was found to be better than that achieved using Ac-Cys-Ala-Ala-Lys(Fc)-Ala-Ala-COOH. Particularly high sensitivities were achieved when using Fc-Lys-Ala-Ala-Cys-NH$_2$ and Fe-Glu-Ala-Ala-Ala-Cys-NH$_2$. Optimal combination of limit of detection and sensitivity was achieved when using Fc-Glu-Ala-Ala-Ala-Cys-NH$_2$.

Example 2: Further Studies of Peptide-Based Electrodes for Biosensing by EIS

Chemical Reagents

1-Ethyl-3-(3-dimethylaminopropyl) carbodiimide (EDC), N-hydroxysuccinimide (NHS) and perchlorate tetrabutylammonium (TBA-ClO$_4$) were purchased from Sigma-Aldrich. Human C-reactive protein (CRP) and human CRP polyclonal antibody (Ab) were also purchased from Sigma-Aldrich, while interleukin-6 (IL-6) and IL-6 Ab were purchased from Rhea Biotech.

The peptide used as support for the receptors was Fc-Glu-Ala-Ala-Cys, manually synthesized by solid phase peptide synthesis using Fmoc protocols on rink amide resin (0.48 mmol g$^{-1}$). Coupling was performed at a 2-fold molar excess relative to the amino component in the resin, using diisopropylcarbodiimide (Dic)/1-hydroxybenzotriazole (HOBt). Fmoc groups were deprotected using 20% 4-methylpiperidine/dimethylformamide (DMF) for 80 min. The ferrocene redox probe was introduced at the N-terminus by reaction with one molar equivalent 3-ferrocenylpropionic anhydride in 5 mL DCM/DMF (1:1) for 24 h. Peptide cleavage was performed by removing side chain protecting groups with 94% trifluoroacetic acid (TFA), 2.5% 1,2-ethanedithiol, 2.5% H$_2$O and 1% triisopropylsilane for 2 h. The peptide was then precipitated with diethyl ether and separated from the reaction solution by centrifugation.

Phosphate buffered saline (PBS) was prepared using the following salt concentrations: 8 g L$^{-1}$NaCl, 0.2 g L$^{-1}$KH$_2$PO$_4$, 1.15 g L$^{-1}$NaH$_2$PO$_4$.12H$_2$O, 0.2 g L$^{-1}$KCl, and 0.2 g L$^{-1}$NaNO$_3$, reaching an expected pH of 7.4.

Brief Description of Receptors and Target Biomarkers

CRP is a protein synthesized by the liver. CRP exists in the form of pentamers with identical protomers, leading to a ~118 kDa protein. CRP, which is present in the blood of healthy individuals, serves as biomarker of inflammation caused by infection or injury, hypertension and cardiovascular diseases. Serum CRP levels exceeding 3.0 mg L$^{-1}$ are indicative of risk of diabetes.

Human IL-6 is a 26 kDa glycoprotein and a member of the cytokine family, which affects the functionalities of the immune system. It is involved in the differentiation process of myeloid cells and in homeostatic and neuroendocrine functions. The overexpression of IL-6 is associated with cardiovascular disease, osteoporosis, diabetes, arthritis and tumors. Increasing interest has focused on the association of IL-6 with cardiovascular disease.

Electrode Pretreatment

Gold electrode surfaces were mechanically polished using aluminum oxide pads (1 µm, 0.3 µm and 0.05 µm) and electrochemically polished in 0.5 M NaOH solution (100 cycles from −1.7 V to −0.7 V at a scan rate of 0.1 V s$^{-1}$). After electrochemical cleaning, the electrodes were immersed in pure ethanol for 30 min. The electrochemical polishing procedure was completed with cyclic voltammetry (CV) scans in 0.5 M H$_2$SO$_4$ solution at 80° C. (50 scans were performed from −0.2 V to 1.5 V at a scan rate of 0.1 V s$^{-1}$). The area of the reduction peak obtained in these CV measurements depends on the active gold surface area. The electroactive area of the polished gold surface can be obtained by using a conversion factor of 410 µC cm$^{-2}$, which is the charge associated with the reduction peak. The ratio of the electro-active area to the geometric area of the electrode (0.03142 cm$^2$) is referred to as the electrochemical surface roughness, which should preferably be kept below 1.5 to ensure reliable and stable molecular film properties.

Electrochemical Measurements

Electrochemical impedance measurements (EIS) were taken in an AUTOLAB potentiostat (from METROHM) equipped with a frequency response analysis (FRA) module using a three-electrode system: a gold disk working electrode (2.0 mm diameter from METROHM, polished as described above), a platinum plate counter electrode and a silver/silver chloride reference electrode (Ag|AgCl, filled with 3.0 M KCl). All the potentials reported in this example are relative to this reference. EIS data were acquired at the formal potential (about 0.45 V) of the redox switches, i.e., ferrocenium/ferrocene redox couple, in frequencies ranging from 1 MHz down to 0.1 Hz, with 20 mV amplitude (peak-to-peak) sinusoidal perturbation. EIS spectra were also examined to ensure the Kramers-Kronig relationship of time-invariance was satisfied. Capacitance spectroscopy diagrams were obtained by converting the complex impedance ($Z^*$) to complex capacitance ($C^*$), using the relationship $C^*(\omega)=1/j\omega Z^*(\omega)$, where $\omega$ is the angular frequency and $j$ is the square root of −1.

CV measurements were taken from −0.0 V to 0.7 V at a scan rate of 0.1 V s$^{-1}$ to determine the formal potential at which impedance spectra were recorded. Electrochemical assay measurements of the chemically modified gold electrodes were taken in 20 mM of TBA-ClO$_4$ dissolved in acetonitrile and water (1:4 v/v) as a supporting electrolyte. The presence of acetonitrile slightly improves redox stability and enables the dissolution of TBA-ClO$_4$. It has been confirmed that TBA-ClO$_4$ has no deleterious influence on specific recognition. Furthermore, in previous studies (Bueno, P. R.; Fernandes, F. C. B.; Davis, J. J. Nanoscale 2017, 9, 15362-15370), the resolved equilibrium binding constant following this protocol was confirmed, within experimental error, to be the same as that observed in PBS solution.

Fabrication of the Biosensing Interface

The redox-active molecular junctions were obtained chemically by immersing the freshly cleaned gold disk electrodes in solutions containing ferrocene redox switches for 16 h at room temperature. Gold electrodes were modified by using solutions of 2 mM of peptides diluted in acetonitrile and water [1:1 (v/v)]. After chemically modifying the electrodes, they were briefly rinsed in deionized water and dried in nitrogen. The chemically modified gold electrodes were then immersed for 30 min in 200 µL of an aqueous solution containing 0.4 M EDC and 0.1 M NHS to activate the carboxylic groups present in peptides, after which they were incubated for 1 h in solutions containing receptors (1 µM in PBS). After the receptors were immobilized, the electrodes were cleaned with PBS, distilled water and dried under nitrogen, prior to characterization by CV and EIS.

Unbound carboxylic groups were blocked with 0.1% BSA solution contained in PBS (pH 7.4) for 30 min. Electrodes modified with peptides containing the redox switches were used to detect human IL-6 glycoprotein or CRP. This was done by immobilizing the IL-6 antibody, the CRP antibody (Ab) or a CRP DNA aptamer on the peptide monolayer. After building the receptive platform, its stability was tested by immersing the electrodes for 30 min in PBS (pH 7.4) and then characterizing them by EIS. This process was repeated three times in each of the assays; those which varied by less than 5% of the blank measurements were considered non-drifting stable assays ready to use.

To test the different assays, solutions were prepared in increasing concentrations of the targets by dropping the electrode for 30 min, followed by cleaning in PBS and distilled water, and drying with nitrogen for subsequent electrochemical measurements. For instance, a receptive interface containing CRP Ab or CRP DNA aptamers immobilized on the redox peptide was used to react with solutions containing CRP in concentrations ranging from 10 pM to 10,000. A redox peptide monolayer was used to support an IL-6 Ab based biorecognition layer, which was used to interact with IL-6 in concentrations ranging from 750 pM to 380,000 pM. All the assays were performed by incubating the target in PBS media. Specificity was ensured by stability tests and a negative control, both performed by successive measurements in PBS (at least three repetitions) in order to ensure stability. The negative control was evaluated specifically by incubation in PBS solutions containing nonspecific proteins such as human serum albumin (HSA), fetuin or BSA in increasing and equivalent concentrations to that used for the detection of the target. No significant variation was found in either stability or negative control tests (within RR<5%).

Assays were carried out with three different working electrodes and standard errors were calculated from these repetitions. The analytical curves were obtained by plotting the relative response in percentage, $$RR\% = \left[\left(\frac{1}{C_{\bar{\mu}target}} - \frac{1}{C_{\bar{\mu}blank}}\right) / \frac{1}{C_{\bar{\mu}blank}}\right] \cdot 100,$$

of $1/C_{\bar{\mu}}$ with respect to the concentration of the targets. $C_{\bar{\mu}}$ was obtained as the real component of the Nyquist capacitance plot. Sensitivity was determined from the slope of the analytical curve constructed using the relationship between RR % and target concentrations.

Results and Discussion

It was hypothesised that the sensitivity of the EIS system to target concentration would depend on the intimacy of access of bound target species to the electrode surface, and hence on the relationship between the relative sizes of the target and receptor species (approximated, for instance, by their relative molecular weights). This principle is schematically illustrated in FIG. 1, which illustrates various conformations and structural configurations. Since sensitivity was predicted to be influenced by the range of the field effect, which in turn is governed by the length scale associated with $1/C_{\bar{\mu}}$, then: a) illustrates cases where an intermediate sensitivity is predicted, while b) illustrates the best expected sensitivity (most intimate access), and c) shows the worst (least intimate access).

To corroborate this hypothesis, experiments were conducted using the peptide-functionalised electrode and to compare: (i) CRP target sensing using either an antibody or aptamer receptor; and (ii) sensing of CRP target or IL-6 target using antibody receptors.

Figure 2:
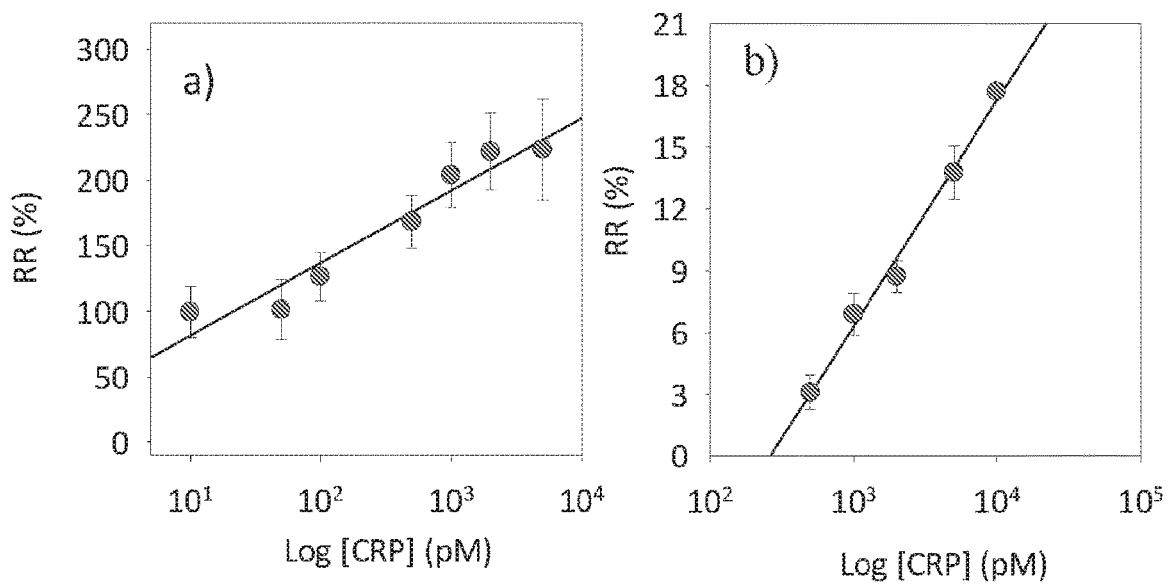
FIG. 2 illustrates the relative response percentage, RR %, of some of the EIS systems described in Example 2 and featuring either an aptamer receptor (panel a) or antibody receptor (panel b) as a function of CRP target concentration (pM).

The RR % as a function of CRP target concentration for (i) is shown in FIG. 2, where it is clear that higher sensitivity was obtained when using an aptamer rather than antibody receptor, and hence when the ratio of target:receptor weights was higher (due to the much lower molecular weight of the aptamer receptor compared with the antibody receptor). For (ii), it was found that the tested Ab-IL-6 receptor protein of 150 kDa could not sensitively detect the small IL-6 target species of only 26 kDa. The results are summarised in Table 2.

TABLE 2

Comparison between performance of electrodes based on different relative target and receptor molecular weights

| Interaction (target/receptor) | Weight ratio (target/receptor) | Sensitivity |
|---|---|---|
| IL-6/IL-6 AB | 0.17 | — |
| CRP/CRP AB | 0.79 | 11 |
| CRP/CRP DNA$_{aptamer}$ | 59.17 | 88 |

Thus, assays systems with greater sensitivity could be obtained by increasing the ratio of the molecular weight of the target species to the molecular weight of the receptor species.

Example 3: Application of the Electrode to Diagnosis of Dengue Virus

EIS measurements were performed using an electrode system constructed and operated in the same manner as in Example 1, with the exception that the receptor species was dengue NS1 antibody for detection of dengue NS1 protein in biological (blood) samples obtained from patients in Sao Paulo, Brazil. The peptide used as support for the receptors was Fc-Glu-Ala-Ala-Cys.

The biological samples used were dengue blood samples (positive or negative). The assay was performed under blinded conditions in which it was not known in advance which samples were positive (i.e., contained dengue NS1 protein indicative of infection in the patient) or negative (did not contain dengue NS1 protein).

Figure 3:
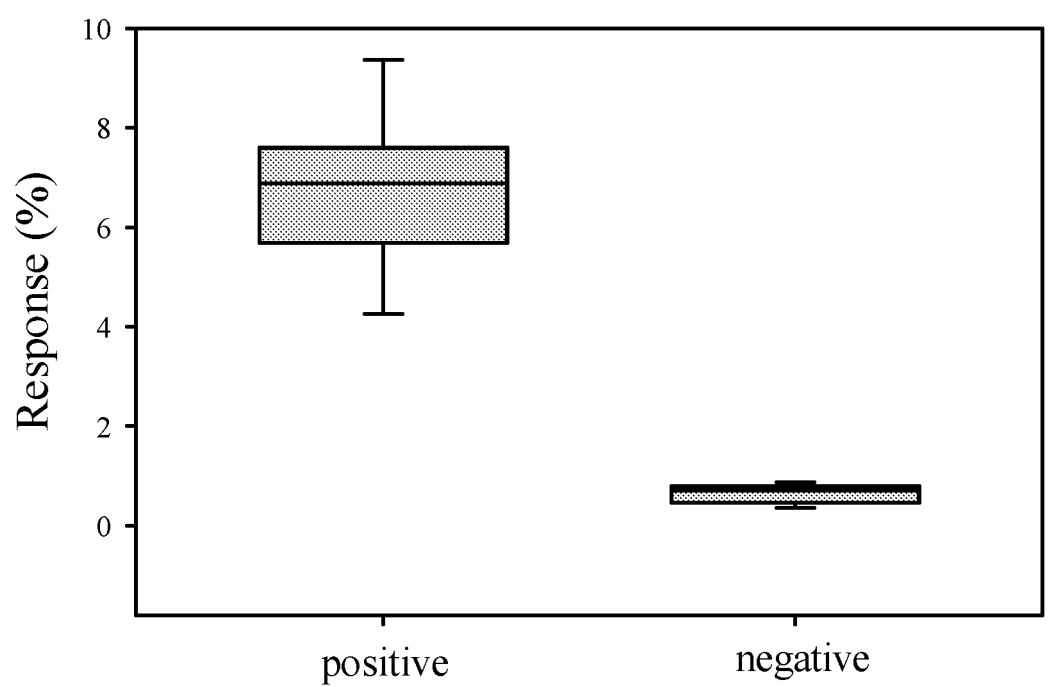
FIG. 3 illustrates the use of the electrochemical capacitance response of peptide monolayers functionalized with NS1 antibodies to discriminate between blinded positive and negative Dengue real blood samples obtained in Sao Paulo (Brazil), as described in more detail in Example 3. The y-axis represents response (%); the left-most bar shows response for positive samples and the right-most bar shows the response for negative samples.

The results are shown in FIG. 3. Response in % corresponds to $[(1/C_{\bar{\mu}target} - 1/C_{\bar{\mu}blank})/1/C_{\bar{\mu}blank}] \cdot 100$. $C_{\bar{\mu}}$ was obtained as the real component of the Nyquist capacitance plot of the impedance spectrum.

As can be seen from FIG. 3, the assay was readily capable clearly and unambiguously of distinguishing between positive and negative samples, i.e. it is suitable for diagnosis of Dengue virus. The success of the assay was attributed at least in part to the following properties of the peptide component of the electrode: (a) its high stability that avoid drift problems that interfere in the detection; and (b) its superior non-fouling properties that avoid non-specific binding.

The invention claimed is:

1. An electrode for use in electrochemical sensing of a target species, which electrode comprises:
   (i) an electrically conductive substrate;
   (ii) a peptide monolayer comprising a plurality of peptide molecules that are each:
      (a) disposed on the substrate;
      (b) attached to a redox active species; and
      (c) attached to a receptor that is capable of binding to the target species;
   wherein:
      the peptide molecules are each from three to five amino acid residues in length, including a first terminal amino acid residue that is adjacent to the substrate and a second terminal amino acid; and
      the redox active species and the receptor are each attached to the second terminal amino acid;
      the attachment to one of the redox active species and the receptor is via a free amine or carboxylic acid group of the second terminal amino acid, and the attachment of the other of the redox active species and the receptor is via a reactive side group present in the second terminal amino acid; and
      in each peptide molecule one of the first terminal amino acid residue and the second terminal amino acid is a C-terminus of the peptide molecule and the other of the first terminal amino acid residue and the second terminal amino acid is an N-terminus of the peptide molecule.

2. The electrode of claim 1, wherein the electrode is for use in electrochemical impedance spectroscopy (EIS) sensing of the target species.

3. The electrode of claim 1, wherein the peptide molecules are each four amino acid residues in length.

4. The electrode of claim 1, wherein the first terminal amino acid residue is a cysteine residue.

5. The electrode of claim 1, wherein the first terminal amino acid residue is the C-terminal amino acid residue of each of the peptide molecules.

6. The electrode of claim 1, wherein the second terminal amino acid is selected from the group consisting of glutamic acid, lysine, aspartic acid, arginine, histidine, cysteine and tyrosine.

7. The electrode of claim 6, wherein the second terminal amino acid is glutamic acid or lysine.

8. The electrode of claim 7, wherein the second terminal amino acid is glutamic acid.

9. The electrode of claim 1, wherein the peptide molecules each have one to three non-terminal amino acid residues between the first terminal amino acid residue and the second terminal amino acid, and wherein the one to three non-terminal amino acid residues comprise one or more alanine residues.

10. The electrode of claim 9, wherein each of the one to three non-terminal amino acid residues is an alanine residue.

11. The electrode of claim 1, wherein the peptide molecules each consists of a sequence selected from the group consisting of Glu-Ala-Ala-Cys, Glu-Ala-Ala-Ala-Cys, Lys-Ala-Ala-Cys and Lys-Ala-Ala-Ala-Cys, where the Cys is one of the C-terminus or the N-terminus of the peptide molecule and the other of the C-terminus and the N-terminus of the peptide molecule is either the Glu or the Lys.

12. The electrode of claim 1, wherein the receptor is selected from the group consisting of aptamers, antibodies, antibody fragments, oligosaccharides, peptides and proteins.

13. The electrode of claim 12, wherein the receptor is an aptamer.

14. The electrode of claim 1, wherein the redox active species is selected from the group consisting of:
(a) a metallic chemical complex comprising a transition metal;
(b) a metallic chemical complex comprising a transition metal that is selected from the group consisting of Fe, Ru, Ti, V, Mn, Cr, Co, Ni, Nb and Mo;
(c) methylene blue; and
(d) ferrocene.

15. The electrode of claim 1, wherein the electrically conductive substrate is a gold substrate.

16. The electrode of claim 1, wherein the target species is an antigen or analyte selected from the group consisting of dengue NS1 protein; angiotensin I converting enzyme (peptidyl-dipeptidase A); adiponectin; advanced glycosylation end product-specific receptor; alpha-2-HS-glycoprotein; angiogenin, ribonuclease, RNase A family, 5; apolipoprotein A-1; apolipoprotein B (including Ag (x) antigen); apolipoprotein E; BCL2-associated X protein; B-cell CLL/lymphoma 2; complement C3; chemokine (C—C motif) ligand 2; CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, clade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, von Willebrand factor, C-reactive protein; glucose; insulin; TRIG; GPT; HSPA1 B; IGFBP2; LEP; ADIPOQ; CCL2; ENG; HP; IL2RA; SCp; SHBG; and TIMP2.

17. The electrode of claim 1, wherein the ratio of the molecular weight of the target species, $M_w^{target}$ (kDa), to the molecular weight of the receptor, $M_w^{receptor}$ (kDa), is:
(i) at least 0.5;
(ii) at least 1.0;
(iii) at least 10; or
(iv) at least 25.

18. The electrode of claim 1, wherein the first terminal amino acid residue that is adjacent to the substrate is the C-terminus of the peptide molecules and the C-terminus of the peptide molecules is amidated.

19. An electrochemical spectrometer comprising the electrode of claim 1.

20. An electrochemical method of sensing a target species, which method comprises:
(A) contacting a carrier medium that may comprise said target species with the electrode of claim 1;
(B) obtaining one or more electrochemical measurements from said electrode; and
(C) determining from said one or more electrochemical measurements whether the target species is present in the carrier medium.

21. The method of claim 20, wherein said electrochemical method is selected from the group consisting of an electrochemical impedance spectroscopy (EIS) method, an electrochemical capacitance spectroscopy (ECS) method, and a method in which step (C) comprises determining the concentration of the target species.

* * * * *